United States Patent [19]

Grollier

[11] Patent Number: 4,971,596
[45] Date of Patent: Nov. 20, 1990

[54] PROCESS FOR DYEING HAIR WITH HYDROXYQUINONE DYES AND METAL SALTS

[75] Inventor: Jean F. Grollier, Paris, France

[73] Assignee: L'Oreal, Paris, France

[21] Appl. No.: 418,932

[22] Filed: Oct. 6, 1989

Related U.S. Application Data

[63] Continuation of Ser. No. 74,719, Jul. 17, 1987.

[30] Foreign Application Priority Data

Jul. 18, 1986 [LU] Luxembourg ............................ 86521

[51] Int. Cl.$^5$ ................................................ A61K 7/13
[52] U.S. Cl. ........................................... 8/424; 8/425; 8/428; 8/429; 8/623; 8/624
[58] Field of Search ................... 8/424, 425, 428, 429, 8/623, 624

[56] References Cited

U.S. PATENT DOCUMENTS

| | | | |
|---|---|---|---|
| 2,338,745 | 1/1944 | Van Riper et al. ...................... | 8/425 |
| 4,601,726 | 7/1986 | Grollier et al. .......................... | 8/410 |
| 4,867,751 | 9/1989 | Lang et al. ............................... | 8/428 |
| 4,888,026 | 12/1989 | Lang et al. ............................... | 8/428 |
| 4,895,575 | 1/1990 | Hocquaux et al. ....................... | 8/424 |

FOREIGN PATENT DOCUMENTS

| | | |
|---|---|---|
| 0133129 | 2/1985 | European Pat. Off. . |
| 2028818 | 6/1970 | Fed. Rep. of Germany . |
| 2119411 | 11/1983 | United Kingdom . |
| 2132642 | 7/1984 | United Kingdom . |

OTHER PUBLICATIONS

Chemical Abstracts, vol. 77, No. 10, 9/4/72, p. 285, Abstract No. 66107m.

Primary Examiner—Paul Lieberman
Assistant Examiner—Christine A. Skane
Attorney, Agent, or Firm—Marshall, O'Toole, Gerstein, Murray & Bicknell

[57] ABSTRACT

Process for dyeing human keratinous fibres, characterized in that there are applied on these fibres, in separate stages, a composition (A) containing a metal salt chosen from copper, iron, cobalt, magnesium, and silver salts, or mixtures thereof, in a cosmetically acceptable medium, and, before or after the application of the composition (A), a composition (B) containing, in a cosmetically acceptable medium, at least one dye corresponding to the formulae:

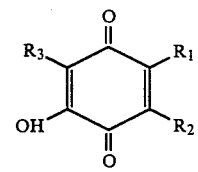

(I)

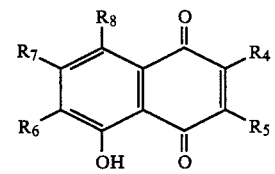

(II)

in which formulae $R_1$ denotes hydrogen or hydroxy, $R_2$ and $r_3$ denote hydrogen, alkyl, alkoxy; $R_4$ denotes hydrogen, hydroxy, alkoxy, alkyl, chlorine; $R_5$ denotes hydrogen, chlorine, alkoxy, hydroxy; and $R_6$, $R_7$ and $R_8$ denote hydrogen or hydroxy.

17 Claims, No Drawings

PROCESS FOR DYEING HAIR WITH HYDROXYQUINONE DYES AND METAL SALTS

This application is a continuation of application Ser. No. 074,719, filed July 17, 1987.

The invention relates to a new process for dyeing hair, and especially living human hair, with hydroxyquinone dyes.

Quinone dyes have been used for a long time for dyeing hair and, in this connection, there may be mentioned henna, the dyeing principle of which, lawsone, was already used by the Egyptians.

French Patent Nos. 2,517,199, 2,517,200 and 2,537,433 describe, moreover, the use of other hydroxynaphthoquinones or hydroxybenzoquinones for the direct dyeing of hair.

In hair dyeing, the capacity for having the widest possible range of coloration is generally sought, in order to obtain natural hues and hues having glints. As a result, the creation of new and powerful hues is in particular demand.

The Applicant has just discovered that it was possible to improve substantially the tinctorial strength or colouring power of certain hydroxyquinone dyes, chosen from hydroxynaphthoquinones and hydroxybenzoquinones, by means of a pre- or post-treatment with a metal salt such as those of copper, iron, cobalt, magnesium and silver.

It was found, in effect, that it was possible to obtain new colorations without a fall in strength by means of combination with a pre- or post-treatment with a metal salt, these colorations being expressed in terms of a difference in hue according to Munsell's notation (ASTM Standard D1535 "Standard Method of Specific Color by the Munsell System") or in Munsell's Book of Color, 1966 Macbeth Color and Photometry Division Kollmorger Corporation Newburgh, N.Y., U.S.A. The colours are designated in Munsell's system by the following formula, HV/C, in which H denotes the hue, V the brightness or value and C the chrominance or "chroma". The Applicant found that it was possible to obtain more intense colours, visualized by a variation in H and V, when a pre- or post-treatment with a metal salt defined above is used, compared with the same dye used without pre- or post-treatment.

The tints thereby obtained possess, moreover, satisfactory light- and washing-fastness.

The subject of the invention is hence a process for dyeing hair, especially living human hair, with certain hydroxyquinone dyes incorporating a pre- or post-treatment with a metal salt.

Another subject of the invention consists of a multicompartment dyeing device or kit which enables the process to be carried out.

Other subjects will emerge on reading the description and examples which follow.

The process according to the invention for dyeing human keratinous fibres, and especially living human hair, is essentially characterized in that the following are applied in separate stages.

a composition (A) containing a metal salt, chosen from copper, cobalt, magnesium, iron and silver salts, or mixtures thereof, in a cosmetically acceptable medium;

and, before or after the composition (A), a composition (B) containing, in a cosmetically acceptable medium, at least one hydroxyquinone dye corresponding to the formulae:

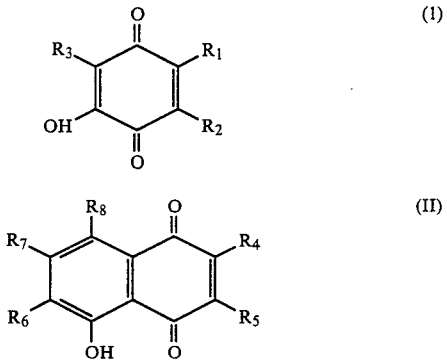

in which formulae:

$R_1$ denotes hydrogen or hydroxy; $R_2$, $R_3$ denote hydrogen, alkyl, alkoxy; $R_4$ denotes hydrogen, hydroxy, alkoxy, alkyl, chlorine; $R_5$ denotes hydrogen, chlorine, alkoxy, hydroxy; and $R_6$, $R_7$ and $R_8$ denote hydrogen or hydroxy.

The alkyl and alkoxy radicals preferably contain 1 to 4 carbon atoms.

The especially preferred dyes are 3-methyl-2,5-dihydroxy-1,4-benzoquinone, 3-methyl-6-methoxy-2,5-dihydroxy-1,4-benzoquinone, 5-hydroxy-1,4-naphthoquinone, 2-methoxy-5-hydroxy-1,4-naphthoquinone and 2,5-dihydroxy-1,4-naphthoquinone.

The dyes are present in the composition used according to the invention in proportions of between 0.05 and 5% by weight relative to the total weight of the composition.

The metal salts are, in particular, chosen from the salts of acids which are acceptable from the cosmetic standpoint, such as, more especially, acetates, sulphates, lactates, glycinates, propionates, butyrates, nitrates and chlorides.

The especially preferred salts are copper, cobalt, iron and silver salts, and mixtures thereof.

The content of metal ion in the composition containing the metal salt is between 0.01 and 2% by weight relative to the total weight of the composition, and preferably between 0.1 and 1%.

The compositions used according to the invention are generally aqueous compositions capable of containing ingredients which are customarily used in cosmetic compositions designed for dyeing hair, such as solvents, surfactants, thickeners, treatment agents, alkalinizing or acidifying agents for adjusting the pH, preservatives, perfumes and the like.

The composition containing the metal salt preferably takes the form of a solution having a pH of between 3 and 11.

The composition containing the hydroxyquinones of formulae I and II, defined above, preferably take the form of a solution thickened to a greater or lesser extent, an emulsion (such as, for example, a cream), a gel, an aerosol foam or any other form suitable for dyeing hair. Its pH is between 3 and 11.

The agents used for adjusting the pH are chosen, more especially, as regards the alkalinizing agents, from alkanolamines and alkali metal or ammonium hydroxides and carbonates. The acidifying agents are preferably chosen from organic or inorganic acids such as lactic acid, acetic acid, tartaric acid, citric acid, phosphoric acid and hydrochloric acid.

The solvents which may be used in these compositions are organic solvents which are acceptable from the cosmetic standpoint, more especially alcohols such as ethyl alcohol, isopropyl alcohol, benzyl alcohol, phenylethyl alcohol or glycols or glycol ethers such as ethylene glycol and its monomethyl, monoethyl or monobutyl ethers, propylene glycol, butylene glycol and dipropylene glycol, as well as the alkyl ethers such as diethylene glycol monobutyl ether, in concentrations of between 0.5 and 75%, and preferably between 2 and 50%, by weight relative to the total weight of each of the compositions.

Surfactants which may be used are anionic, cationic, nonionic or amphoteric surfactants, or mixtures thereof. These agents are preferably used in proportions of between 0.1 and 50% by weight, and advantageously between 1 and 20% by weight, relative to the total weight of the composition. Among surfactants, there may be mentioned anionic agents such as alkali metal salts, magnesium salts, ammonium salts, amine salts and alkanolamine salts of the following compounds: alkyl sulphates, alkyl ether sulphates, alkylamide sulphates, ethoxylated or otherwise, alkylamide sulphonates, alpha-olefin sulphonates and alkyl sulphoacetates; the alkyl radicals in these compounds having 12 to 18 carbon atoms.

It is also possible to use the abovementioned salts of fatty acids such as lauric, myristic, oleic, ricinoleic, palmitic and stearic acids, hydrogenated coconut oil acids and polyglycol ether carboxylic acids.

By way of cationic surfactants, there may be used, in particular, fatty amine salts, quaternary ammonium salts such as alkyldimethylbenzylammonium and dimethyldialkylammonium chlorides and bromides, alkylpyridinium salts and imidazoline derivatives. The alkyl groups in the abovementioned quaternary ammonium derivatives are long-chain groups preferably having between 12 and 18 carbon atoms. Among these compounds of cationic nature, amine oxides may also be mentioned.

The amphoteric surfactants which may be used are, in particular, alkylamino(mono- and di)propionates, betaines such as alkylbetaines, N-alkylsulphobetaines and N-alkylaminobetaines, the alkyl radical having between 8 and 22 carbon atoms, and cycloimidinium compounds such as alkylimidazolines.

The nonionic surfactants which may be used in compositions employed according to the invention may be chosen, more especially, from:

(a) the products of condensation of a monohydric alcohol, an α-diol, an alkylphenol or an amide with glycidol or a glycidol precursor corresponding, in particular, to the formula:

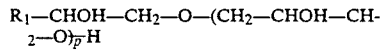

in which $R_1$ denotes an aliphatic, cycloaliphatic or arylaliphatic radical, preferably having between 7 and 21 carbon atoms, and mixtures thereof, the aliphatic chains being capable of containing ether, thioether or hydroxymethylene groups, and p has a value of between 1 and 10 inclusive. Especially preferred compounds are those in which $R_1$ denotes a mixture of alkyl radicals having between 9 and 12 carbon atoms and p has a statistical value of 3.5, or alternatively those in which $R_1$ denotes $C_{10}$ alkyl radical and p has a statistical value of 2.5. Such compounds are described, in particular, in French Patent No. 2,091,516.

b) compounds corresponding to the formula:

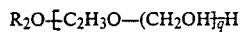

in which $R_2$ denotes an alkyl, alkenyl or alkylaryl radical and q has a statistical value of between 1 and 10. The preferred compounds are those in which $R_2$ denotes a $C_{12}H_{25}$ group and q has a statistical value of 4 to 5. These compounds are described, in particular, in French Patent No. 1,477,048.

(c) compounds corresponding to the formula:

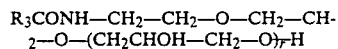

in which $R_3$ denotes a saturated or unsaturated, linear or branched aliphatic radical or mixture of such radicals, optionally capable of containing one or more hydroxyl groups and having between 8 and 30 carbon atoms, of natural or synthetic origin, and r denotes an integer or decimal number from 1 to 5 and represents the average degree of condensation; the especially preferred compounds are those in which $R_3$ denotes a mixture of radicals derived from lauric, myristic, oleic or coconut acids and r has a statistical value of 3 to 4. Such compounds are described, more especially, in French Patent No. 2,328,763.

(d) polyethoxylated or polyglycerolated alcohols, alkylphenols or fatty acids having a $C_8$ to $C_{18}$ fatty chain, condensates of ethylene oxide and propylene oxide with fatty alcohols; polyethoxylated fatty amides containing at least 5 moles of ethylene oxide, and polyethoxylated fatty amines.

The compositions used according to the invention can also contain amides such as the mono- and diethanolamides of fatty acids derived from coconut, of lauric acid or of oleic acid, in concentrations of between 0.05 and 10% by weight relative to the total weight of the composition.

The thickening agents which can be added to the compositions used according to the invention are preferably chosen from sodium alginate, gum arabic, xanthan gum, guar gum, cellulose derivatives such as methylcellulose, hydroxyethylcellulose, hydroxypropylmethylcellulose and the sodium salt of carboxymethylcellulose, and acrylic acid polymers. It is also possible to use inorganic thickening agents such as bentonite. These thickeners are used alone or mixed, and are preferably present in proportions of between 0.1 and 5% by weight relative to the total weight of each of the compositions, and advantageously between 0.2 and 3% by weight.

The compositions according to the invention can contain other direct dyes, and among the latter there may be mentioned nitro derivatives of the benzene series, and anthraquinone and azo dyes, and natural dyes other than the hydroxybenzoquinones and hydroxynaphthoquinones of formulae I and II.

Another embodiment of the invention consists in preparing the composition containing the dyes of formulae I and II in anhydrous form and in the presence of organic solvents defined above, the composition containing less than 1% of water, and in preparing at the time of use the aqueous composition corresponding to the definition given above. This variant is especially advantageous when the dye is unstable in aqueous medium.

These anhydrous compositions can contain, in addition, anhydrous nonionic surfactants as described in French Patent Application No. 83/07,045.

The composition containing the dyes of formulae I and II can also be packaged in the form of a mixture of powders comprising, on the one hand the dyes of formulae I and II or the natural products reduced to powder containing them, and on the other hand flours, starchy or mucilagineous substances, silicas, powdered plants, clays or plants powdered after extraction of their active principles. Such a composition is diluted with water or a solvent or an oil which is cosmetically acceptable, so as to obtain a product also known as a "cataplasm" having a viscosity of 0.1 to 9 Pa.s. The composition containing the metal salt is preferably applied on the hair before the application of the cataplasm.

The process according to the invention is preferably carried out by applying on the human keratinous fibres, in separate stages, the composition A containing the metal salt at a pH of between 3 and 11 for a period of 3 to +minutes, and more especially from 5 to 10 minutes, and the composition B containing the dyes of the hydroxybenzoquinone or hydroxynaphthoquinone family of formulae I and/or II defined above, this second composition being maintained in contact with the hair for a Period of 3 to 40 minutes, and preferably from 5 to 30 minutes, the hair then being rinsed, optionally washed and dried.

The composition A is applied either before or after the composition B, the hair being rinsed between the two applications.

An especially advantageous embodiment of the invention consists in presenting the compositions used in the process in a multi-compartment device, also known as a "dyeing kit", incorporating in one of the compartments the composition containing the metal salt in a cosmetically acceptable medium, and in the other compartment a composition containing the hydroxybenzoquinones or hydroxynaphthoquinones corresponding to the formulae I and II defined above in a cosmetically acceptable medium. A third compartment can be provided when the composition containing the dyes is anhydrous, the latter compartment containing the aqueous cosmetic vehicle.

The examples which follow are designed to illustrate the invention without thereby being limiting in nature.

EXAMPLE 1

The following compositions are prepared:

| COMPOSITION A | |
|---|---|
| $CuSO_4.5H_2O$ | 1 g |
| Monoethanolamine | qs pH 9.3 |
| Water | qs 100 g |
| COMPOSITION B | |
| 2,5-Dihydroxy-3-methyl-1,4-benzoquinone | 0.5 g |
| Butyldiglycol | 50 g |
| Sodium carbonate | qs pH 3 |
| Water | qs 100 g |

The composition A is applied for 5 minutes on hair which is 90% white; it is rinsed and the composition B is applied and left in place for 30 minutes. After rinsing, a pearly golden brown hue is obtained.

This composition can be packaged in a dyeing kit incorporating two compartments which contain the compositions A and B, respectively.

Example 2

The following compositions are prepared:

| COMPOSITION A | |
|---|---|
| $CuSO_4.5H_2O$ | 0.5 g |
| Sodium alkyl ether sulphate, 0.6 meq/g | 5 g |
| Xanthan gum sold under the name "RHODOPOL 23 SC" by RHONE POULENC | 0.32 g |
| $NH_4OH$ | qs pH 10.8 |
| Water | qs 100 g |
| COMPOSITION B | |
| 2,5-Dihydroxy-1,4-naphthoquinone | 0.2 g |
| 2-Methoxy-5-hydroxy-1,4-naphthoquinone | 0.15 g |
| Nonylphenol oxyethyleneated with 9 moles of ethylene oxide | 10 g |
| Butyldiglycol | 50 g |
| Ethyl alcohol | 10 g |
| Monoethanolamine | qs pH 5 |
| Water | qs 100 g |

The composition A is applied for 10 minutes on hair which is 90% white. It is rinsed and the dyeing composition B is applied and left in place for 20 minutes. After rinsing, a pearly beige blond coloration is obtained.

Tables I to IV below illustrate the use of aqueous dyeing compositions (B).

Examples 3 and 6 to 15 inclusive illustrate a post-treatment with a metal salt, that is to say, in these examples, the composition B is applied on the hair for 30 minutes, the hair is rinsed and the composition A is applied and left in place for 5 minutes. After rinsing, the indicated hue is obtained.

Examples 4 and 5 and 16 to 28 inclusive illustrate a pretreatment with a metal salt, that is to say, in these examples, the composition A is applied for 5 minutes; the hair is rinsed and the composition B is applied and left in place for 30 minutes. After rinsing, the indicated hue is obtained.

TABLE I

| Example No. | 3 | 4 | 5 | 6 | 7 | 8 | 9 |
|---|---|---|---|---|---|---|---|
| Composition A | | | | | | | |
| $CuSO_4.5H_2O$ | | | | 1 g | | 1 g | 1 g |
| $Cu(NO_3)_2$ | 1 g | 1 g | | | 1 g | | |
| Cupric acetate | | | 1 g | | | | |
| Monoethanolamine qs pH: | 9 | | 9 | 9 | 9 | | 9 |
| Lactic acid qs pH: | | 4 | | | | 4 | |
| Water qs g | 100 | 100 | 100 | 100 | 100 | 100 | 100 |
| Composition B | | | | | | | |
| 2,5-Dihydroxynaphthoquinone | 0.5 g | 0.5 g | 0.5 g | | | | |
| 3-Methyl-6-methoxy- | | | | 0.5 g | 0.5 g | 0.5 g | 0.5 g |

TABLE I-continued

| Example No. | 3 | 4 | 5 | 6 | 7 | 8 | 9 |
|---|---|---|---|---|---|---|---|
| 2,5-dihydroxybenzoquinone | | | | | | | |
| Butyldiglycol | 50 g | 50 g | 50 g | 50 g | 50 g | 50 g | 50 g |
| Monoethanolamine qs pH: | 9 | 9 | 9 | | | | |
| Lactic acid qs pH: | | | | 4 | 4 | 4 | 4 |
| Water qs g | 100 | 100 | 100 | 100 | 100 | 100 | 100 |
| Coloration obtained on 90% white natural hair | | | | pale olive-grey | pale olive-grey | | |
| On 90% white permanent-waved hair | greyish red-brown | pale brown | medium red-brown | | | dark yellow | greyish olive |

TABLE II

| Example No. | 10 | 11 | 12 | 13 | 14 | 15 | 16 |
|---|---|---|---|---|---|---|---|
| Composition A | | | | | | | |
| $CuSO_4.5H_2O$ | | | | | | | 1 g |
| $CuCl_2$ | | | 1 g | 1 g | | | |
| $Cu(NO_3)_2$ | 1 g | 1 g | | | | | |
| Cupric acetate | | | | | 1 g | 1 g | |
| Monoethanolamine qs pH: | | 9 | | 9 | | 9 | |
| Lactic acid qs pH: | 4 | | 4 | | 4 | | 4 |
| Water qs g | 100 | 100 | 100 | 100 | 100 | 100 | 100 |
| Composition B | | | | | | | |
| 3-Methyl-6-methoxy-2,5-dihydroxybenzoquinone | 0.5 g | 0.5 g | 0.5 g | 0.5 g | 0.5 g | 0.5 g | 0.5 g |
| Butyldiglycol | 50 g | 50 g | 50 g | 50 g | 50 g | 50 g | 50 g |
| Lactic acid qs pH: | 4 | 4 | 4 | 4 | 4 | 4 | 4 |
| Water qs g | 100 | 100 | 100 | 100 | 100 | 100 | 100 |
| Coloration obtained on 90% white permanent-waved hair | medium olive | greyish olive | medium olive | olive-grey | pale olive-brown | olive-grey | medium olive |

TABLE III

| Example No. | 17 | 18 | 19 | 20 | 21 | 22 |
|---|---|---|---|---|---|---|
| Composition A | | | | | | |
| $CuSO_4.5H_2O$ | 1 g | | | | | |
| $CuCl_2$ | | | | 1 g | 1 g | |
| $Cu(NO_3)_2$ | | 1 g | 1 g | | | |
| Cupric acetate | | | | | | 1 g |
| Monoethanolamine qs pH: | 9 | | 9 | | 9 | |
| Lactic acid qs pH: | | 4 | | 4 | | 4 |
| Water qs g | 100 | 100 | 100 | 100 | 100 | 100 |
| Composition B | | | | | | |
| 3-Methyl-6-methoxy-2,5-dihydroxybenzoquinone | 0.5 g | 0.5 g | 0.5 g | 0.5 g | 0.5 g | 0.5 g |
| Butyldiglycol | 50 g | 50 g | 50 g | 50 g | 50 g | 50 g |
| Lactic acid qs pH: | 4 | 4 | 4 | 4 | 4 | 4 |
| Water qs g | 100 | 100 | 100 | 100 | 100 | 100 |
| Coloration obtained on 90% white permanent-waved hair | pale olive | pale olive-brown | medium olive | medium olive | medium olive | medium olive-brown |

TABLE IV

| Example No. | 23 | 24 | 25 | 26 | 27 | 28 |
|---|---|---|---|---|---|---|
| Composition A | | | | | | |
| Cupric acetate | 1 g | | | | | |
| $CoCl_2$ | | 1 g | | | | |
| Mg acetate | | | 1 g | | | |
| $FeCl_2$ | | | | | 1 g | 1 g |
| $AgNO_3$ | | | | 1 g | | |
| Monoethanolamine qs pH: | 9 | | | | | |
| Lactic acid qs pH: | | 4 | 4 | 4 | 4 | 4 |
| Water qs g | 100 | 100 | 100 | 100 | 100 | 100 |
| Composition B | | | | | | |
| 3-Methyl-6-methoxy-2,5-dihydroxybenzoquinone | 0.5 g | 0.5 g | 0.5 g | 0.5 g | 0.5 g | 0.5 g |

TABLE IV-continued

| Example No. | 23 | 24 | 25 | 26 | 27 | 28 |
|---|---|---|---|---|---|---|
| Butyldiglycol | 50 g | 50 g | 50 g | 50 g | 50 g | 50 g |
| Monoethanolamine qs pH: | | | | | | 9 |
| Lactic acid qs pH: | 4 | 4 | 4 | 4 | 4 | |
| Water qs g | 100 | 100 | 100 | 100 | 100 | 100 |
| Coloration obtained on 90% white permanent-waved hair | medium olive | medium yellow-brown | grey yellow-brown | pale olive-brown | dark red | medium yellow-brown |

Tables V and VI below illustrate the use of dyes in an anhydrous medium.

In Examples Nos. 29 to 43, the composition (A) is applied for 5 minutes on the hair; it is rinsed and the composition B, diluted with water in the ratio 1:1.5 by weight, is applied. It is left in place for 30 minutes and the hair is rinsed.

Tables VII and VIII below illustrate the use of a colouring cataplasm.

In Examples 44 to 57, the composition (A) is applied for 5 minutes on the hair, it is rinsed and the composition (B), diluted with water in the ratio 1:3 by weight, is applied. It is left in place for 30 minutes and the hair is rinsed.

TABLE V

| Example No. | 29 | 30 | 31 | 32 | 33 | 34 | 35 | 36 |
|---|---|---|---|---|---|---|---|---|
| Composition A | | | | | | | | |
| $CuSO_4.5H_2O$ | 1 g | | | 1 g | 1 g | | | |
| $CuCl_2$ | | 1 g | | | | | | 1 g |
| $Cu(NO_3)_2$ | | | | | | 1 g | 1 g | |
| $AgNO_3$ | | | 1 g | | | | | |
| Monoethanolamine qs pH: | 9 | 9 | | | 9 | | 9 | |
| Lactic acid qs pH: | | | 4 | 4 | | 4 | | 4 |
| Water qs g | 100 | 100 | 100 | 100 | 100 | 100 | 100 | 100 |
| Composition B | | | | | | | | |
| 2,5-Dihydroxynaphtho-quinone | 1.25 g | 1.25 g | 1.25 g | | | | | |
| 3-Methyl-6-methoxy-2,5-dihydroxybenzoquinone | | | | 1.25 g | 1.25 g | 1.25 g | 1.25 g | 1.25 g |
| Ethanolamine derivative (AMIETOL M 21) | 1 g | 1 g | 1 g | | | | | |
| Lactic acid | | | | 1 g | 1 g | 1 g | 1 g | 1 g |
| Ethyl alcohol g | 28.5 | 28.5 | 28.5 | 28.5 | 28.5 | 28.5 | 28.5 | 28.5 |
| Nonylphenol oxyethyleneated with 9 moles of ethylene oxide, qs g | 100 | 100 | 100 | 100 | 100 | 100 | 100 | 100 |
| Coloration obtained on 90% white natural hair | grey-brown | pale brown | medium brown | | | | | |
| On 90% white permanent-waved hair | | | | dark grey-brown | medium olive | medium olive-brown | medium olive | medium olive-brown |

TABLE VI

| Example No. | 37 | 38 | 39 | 40 | 41 | 42 | 43 |
|---|---|---|---|---|---|---|---|
| Composition A | | | | | | | |
| $CuCl_2$ | 1 g | | | | | | |
| Cupric acetate | | 1 g | 1 g | | | | |
| $CoCl_2$ | | | | 1 g | | | |
| Mg acetate | | | | | 1 g | | |
| $FeCl_2$ | | | | | | 1 g | |
| $AgNO_3$ | | | | | | | 1 g |
| Monoethanolamine qs pH: | 9 | | 9 | | | | |
| Lactic acid qs pH: | | 4 | | 4 | 4 | 4 | 4 |
| Water qs g | 100 | 100 | 100 | 100 | 100 | 100 | 100 |
| Composition B | | | | | | | |
| 3-Methyl-6-methoxy-2,5-dihydroxybenzoquinone g | 1.25 | 1.25 | 1.25 | 1.25 | 1.25 | 1.25 | 1.25 |
| Amietol M 21 | | | | | | | 1 g |
| Lactic acid | | 1 g | 1 g | 1 g | 1 g | 1 g | 1 g |
| Ethyl alcohol g | 28.5 | 28.5 | 28.5 | 28.5 | 28.5 | 28.5 | 28.5 |
| Nonylphenol oxyethyleneated with 9 moles of ethylene oxide, qs g | 100 | 100 | 100 | 100 | 100 | 100 | 100 |
| Coloration obtained on 90% white natural hair | | | | | | | medium red-brown |
| On 90% white permanent-waved hair | medium olive | medium olive-brown | medium olive | grey red-brown | dark grey-violet | dark grey-brown | |

TABLE VII

| Example No. | 44 | 45 | 46 | 47 | 48 | 49 | 50 |
|---|---|---|---|---|---|---|---|
| Composition A | | | | | | | |
| $CuSO_4.5H_2O$ | 1 g | 1 g | | | | | |
| $CuCl_2$ | | | | | 1 g | 1 g | |
| $Cu(NO_3)_2$ | | | 1 g | 1 g | | | |
| Cupric acetate | | | | | | | 1 g |
| Monoethanolamine qs pH: | | 9 | | 9 | | 9 | |
| Lactic acid qs pH: | 4 | | 4 | | 4 | | 4 |
| Water qs g | 100 | 100 | 100 | 100 | 100 | 100 | 100 |
| Composition B | | | | | | | |
| 3-Methyl-6-methoxy-2,5-dihydroxybenzoquinone | 2 g | 2 g | 2 g | 2 g | 2 g | 2 g | 2 g |
| Powdered residues of exhaustive extraction of Saponaria, of particle size <80μ | 35 g | 35 g | 35 g | 35 g | 35 g | 35 g | 35 g |
| Maize cobs | 15 g | 15 g | 15 g | 15 g | 15 g | 15 g | 15 g |
| Lactic acid | 4 g | 4 g | 4 g | 4 g | 4 g | 4 g | 4 g |
| Carob gum sold under the name "VIDOGUM L 175" by UNIPECTINE | 3 g | 3 g | 3 g | 3 g | 3 g | 3 g | 3 g |
| Fat-free soluble powdered milk qs g | 100 | 100 | 100 | 100 | 100 | 100 | 100 |
| Coloration obtained on 90% white permanent-waved hair | medium olive brown | medium olive | grey yellow-brown | medium olive | medium olive | medium olive | medium olive-brown |

TABLE VIII

| Example No. | 51 | 52 | 53 | 54 | 55 | 56 | 57 |
|---|---|---|---|---|---|---|---|
| Composition A | | | | | | | |
| $CuCl_2$ | | | | | | 1 g | |
| $FeCl_2$ | | | | | | | 1 g |
| Cupric acetate | 1 g | | | | | | |
| $CoCl_2$ | | 1 g | | | | | |
| Mg acetate | | | 1 g | | | | |
| $AgNO_3$ | | | | 1 g | 1 g | | |
| Monoethanolamine qs pH: | 9 | | | | | 9 | |
| Lactic acid qs pH: | | 4 | 4 | 4 | 4 | | |
| Water qs g | 100 | 100 | 100 | 100 | 100 | 100 | 100 |
| Composition B | | | | | | | |
| 2,5-Dihydroxynaphthoquinone | | | | | | 2 g | 2 g |
| 3-Methyl-6-methoxy-2,5-dihydroxybenzoquinone | 2 g | 2 g | 2 g | 2 g | 2 g | | |
| Powdered residues of exhaustive extraction of Saponaria, of particle size <80μ | 35 g | 35 g | 35 g | 35 g | 30 g | 30 g | 30 g |
| Maize cobs | 15 g | 15 g | 15 g | 15 g | 50 g | 50 g | 50 g |
| Lactic acid | 4 g | 4 g | 4 g | 4 g | | | |
| Anhydrous pure $Na_2CO_3$ | | | | | 3 g | 3 g | 3 g |
| Carob gum sold under the name "VIDOGUM L 175" by UNIPECTINE | 3 g | 3 g | 3 g | 3 g | | | |
| Fat-free soluble powdered milk qs g | 100 | 100 | 100 | 100 | 100 | 100 | 100 |
| Coloration obtained on 90% white natural hair | | | | | | medium red-brown | |
| 90% white permanent-waved hair | medium olive | medium brown | grey-violet | grey red-brown | grey red-brown | | dark red-brown |

EXAMPLE 58

| Composition A | |
|---|---|
| $CuSO_4.5H_2O$ | 1 g |
| Monoethanolamine qs | pH 9.3 |
| Water qs | 100 g |
| Composition B | |
| 5-Hydroxy-1,4-naphthoquinone | 0.5 g |
| Butyldiglycol | 50 g |
| Water qs | 100 g |
| pH 5.1 | |

Composition (A) is applied for 5 minutes on natural 90% white hair; it is rinsed and the composition (B) is applied for 30 minutes. After rinsing, the hair is coloured chestnut-brown.

What is claimed is:

1. Process for dyeing human keratinous fibers, wherein there are applied to these fibers, in separate stages, a composition A comprising a metal salt selected from the group consisting of copper, $Fe^{2+}$, cobalt, and silver salts, and mixtures thereof, in a cosmetically-acceptable medium, and, before or after the application of composition A, a composition B comprising, in a cosmetically-acceptable medium, at least one dye corresponding to either one of the formulae:

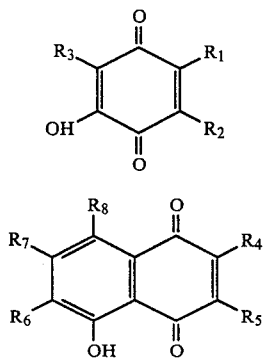

in which formulae $R_1$ represents hydrogen or hydroxy; $R_2$ and $R_3$ represent hydrogen, alkyl, or alkoxy; $R_4$ represents hydrogen, hydroxy, alkoxy, alkyl, or chlorine; $R_5$ represents hydrogen, chlorine, alkoxy, or hydroxy; and $R_6$, $R_7$, and $R_8$ represent hydrogen or hydroxy.

2. Process according to claim 1, wherein said dye is selected from 3-methyl-2,5-dihydroxy-1,4-benzoquinone, 3-methyl-6-methoxy-2,5-dihydroxy-1,4-benzoquinone, 5-hydroxyl-1,4-naphthoquinone, 2-methoxy-5-hydroxy-1,4-naphthoquinone and 2,5-dihydroxy-1,4-naphthoquinone.

3. Process according to claim 1 wherein said metal salt is selected from cupric acetate, $CuSO_4$, $Cu(NO_3)_2$, $CuCl_2$, $FeCl_2$, $CoCl_2$, $AgNO_3$, and mixtures thereof.

4. Process according to claim 1 wherein said metal salt in composition A contains said metal in proportions of between 0.01 and 2% by weight relative to the total weight of the composition.

5. Process according to claim 1 wherein said dye is present in composition B in proportions of between 0.05 and 5% by weight relative to the total weight of the composition.

6. Process according to claim 1 wherein composition A is applied at a pH of between 3 and 11 for 3 to 30 minutes, and composition B is applied for 3 to 40 minutes, said fibers being rinsed between the two applications.

7. Process according to claim 1 wherein said compositions A and B take the form of thickened or gelled liquids, emulsions, aerosol foams or a mixture of powders to be diluted before use.

8. Process according to claim 1 wherein compositions A and B are aqueous compositions additionally containing cosmetically-acceptable ingredients chosen from solvents, surfactants, thickeners, treatment agents, alkalinizing or acidifying agents, preservatives and perfumes.

9. Process according to claim 8 wherein said solvents are chosen from alcohols, glycols, glycol ethers, and alkyl ethers, and are present in proportions of between 0.5 and 75% by weight relative to the total weight of the composition.

10. Process according to claim 1 wherein compositions A and B contain at least one anionic, cationic, nonionic or amphoteric surfactant, or mixtures thereof, in proportions of 0.1 to 50% by weight, relative to the total weight of the composition.

11. Process according to claim 1 wherein at least one of said compositions A and B contains a fatty acid amide or mixtures thereof in a proportion of 0.5 to 10% by weight.

12. Process according to claim 1 wherein at least one of said compositions A and B additionally contains one or more thickening agents in proportions of 0.1 to 5% by weight.

13. Process according to claim 1 wherein composition B additionally contains a dye selected from nitro derivatives of the benzene series, anthraquinone, azo dyes, or natural dyes other than hydroxybenzoquinones or hydroxynaphthoquinones of the formulae (I) or (II).

14. Process according to claim 1 wherein composition B is in anhydrous form in a cosmetically-acceptable solvent, said composition being mixed immediately before use with a cosmetically acceptable aqueous medium.

15. Process according to claim 1 wherein composition A is applied in a first stage, and composition B is applied in a second stage, composition B having a viscosity of 0.1 to 9 Pa.s resulting from dilution with water, a cosmetically-acceptable solvent oil, or a powder containing said dye and flours or starchy or mucilaginous substances, silicas, plants powdered after extraction of their active principles, clays or powdered plants.

16. Multi-compartment kit for use in dyeing human keratinous fibers which comprises, in a first compartment, composition A and, in a second compartment, composition B, as defined in claim 1.

17. Multi-compartment kit for use in dyeing human keratinous fibers which comprises, in a first compartment, composition A, and, in a second compartment, composition B in anhydrous form, composition A and composition B being as defined in claim 1, and in a third compartment an ingredient or a mixture of ingredients selected from solvents, surfactants, thickeners, treatment agents, alkalinizing or acidifying agents, preservatives and perfumes, in a cosmetically-acceptable aqueous medium.

* * * * *